US012810981B2

(12) United States Patent
Jing et al.

(10) Patent No.: US 12,810,981 B2
(45) Date of Patent: Nov. 24, 2026

(54) METHOD FOR GENERATING TREATMENT PLAN, COMPUTER DEVICE, AND STORAGE MEDIUM

(71) Applicants: SHENZHEN OUR NEW MEDICAL TECHNOLOGIES DEVELOPMENT CO., LTD., Shenzhen (CN); OUR UNITED CORPORATION, Xi'an (CN)

(72) Inventors: Yipeng Jing, Xi'an (CN); Xikang Zhao, Xi'an (CN)

(73) Assignees: SHENZHEN OUR NEW MEDICAL TECHNOLOGIES DEVELOPMENT CO., LTD., Shenzhen (CN); OUR UNITED CORPORATION, Xi'an (CN)

( * ) Notice: Subject to any disclaimer, the term of this patent is extended or adjusted under 35 U.S.C. 154(b) by 229 days.

(21) Appl. No.: 18/321,658

(22) Filed: May 22, 2023

(65) Prior Publication Data

US 2023/0377704 A1 Nov. 23, 2023

(30) Foreign Application Priority Data

May 23, 2022 (CN) ........................ 202210566912.X

(51) Int. Cl.

| | |
|---|---|
| ***G06Q 50/00*** | (2024.01) |
| ***G06T 7/30*** | (2017.01) |
| ***G16H 20/00*** | (2018.01) |
| ***G16H 30/20*** | (2018.01) |

(52) U.S. Cl.

CPC ............... *G16H 20/00* (2018.01); *G06T 7/30* (2017.01); *G16H 30/20* (2018.01); *G06T 2207/10081* (2013.01)

(58) Field of Classification Search

CPC ........... G16H 20/00; G16H 30/20; G06T 7/30

See application file for complete search history.

(56) References Cited

U.S. PATENT DOCUMENTS

| | | | | |
|---|---|---|---|---|
| 2009/0156906 A1* | 6/2009 | Liebman | ................ | G16H 50/50 600/300 |
| 2011/0317887 A1* | 12/2011 | Huber | .................... | G16H 30/20 382/128 |
| 2023/0017353 A1* | 1/2023 | Bai | ...................... | A61N 5/1082 |

FOREIGN PATENT DOCUMENTS

| | | | |
|---|---|---|---|
| CN | 102306239 A | 1/2012 | |
| CN | 106920234 A | 7/2017 | |
| CN | 109771850 A | 5/2019 | |
| CN | 111481839 A | 8/2020 | |
| CN | 112546461 A | 3/2021 | |
| CN | 113573776 A * | 10/2021 | ........... A61N 5/1039 |

(Continued)

*Primary Examiner* — Rajesh Khattar

(74) *Attorney, Agent, or Firm* — Kolitch Romano Dascenzo Gates LLP

(57) ABSTRACT

The present disclosure discloses a method for generating a treatment plan. The method includes: acquiring a first image of a target object, wherein the first image does not contain positioning information of the target object; generating a first treatment plan for the target object based on the first image; acquiring a second image of the target object, wherein the second image contains the positioning information of the target object; registering the first image and the second image; and generating a second treatment plan by updating the first treatment plan in response to a registration result.

18 Claims, 4 Drawing Sheets

(56) References Cited

FOREIGN PATENT DOCUMENTS

| | | | | |
|---|---|---|---|---|
| CN | 114446440 | A | 5/2022 | |
| WO | WO-2021184161 | A1 * | 9/2021 | ........... A61N 5/1071 |

* cited by examiner

METHOD FOR GENERATING TREATMENT PLAN, COMPUTER DEVICE, AND STORAGE MEDIUM

CROSS-REFERENCE TO RELATED APPLICATION

This application is based on and claims priority to Chinese Patent Application No. 202210566912.X, filed on May 23, 2022, and entitled “TREATMENT PLAN GENERATION METHOD, COMPUTER EQUIPMENT AND STORAGE MEDIUM,” the disclosure of which is herein incorporated by reference in its entirety.

TECHNICAL FIELD

The present disclosure relates to the field of radiation therapy technologies, and in particular, to a method for generating a treatment plan, a computer device, and a storage medium.

BACKGROUND OF THE INVENTION

Radiation therapy is a common form of tumor treatment, and in the radiation therapy, tumor lesions are killed using high-energy radiations generated by a radiation device.

Generally, in performing the radiation treatment on a tumor of a patient, a radiation treatment plan is made first based on the tumor of the patient, and then an expected dose of radiation is applied to the tumor of the patient based on the radiation treatment plan by the radiation device to treat the tumor of the patient.

SUMMARY OF THE INVENTION

Embodiments of the present disclosure provide a method for generating a treatment plan, a computer device, and a storage medium.

Some embodiments of the present disclosure provide a method for generating a treatment plan. The method includes:

acquiring a first image of a target object, wherein the first image does not contain positioning information of the target object; generating a first treatment plan for the target object based on the first image; acquiring a second image of the target object, wherein the second image contains the positioning information of the target object; registering the first image and the second image; and generating a second treatment plan for the target object by updating the first treatment plan in response to a registration result.

In some embodiments of the present disclosure, the registration result includes a rotation offset amount and/or a translation offset amount.

In some embodiments of the present disclosure, generating the second treatment plan for the target object by updating the first treatment plan in response to the registration result includes:

generating the second treatment plan for the target object by modifying corresponding treatment parameters in the first treatment plan based on the rotation offset amount and/or the translation offset amount.

In some embodiments of the present disclosure, both the first image and the second image are images of the target object acquired prior to a treatment stage.

In some embodiments of the present disclosure, the first image is an image of the target object acquired prior to a treatment stage; and the second image is an image of the target object acquired in the treatment stage.

In some embodiments of the present disclosure, the first treatment plan includes an image guidance parameter and a treatment parameter; and prior to acquiring the second image of the target object, the method further includes:

Instructing, by outputting the first treatment plan only containing the image guidance parameter, a radiation device to perform image guidance on the target object to generate the second image of the target object.

In some embodiments of the present disclosure, the second image is a CBCT image of the target object acquired in the treatment stage.

In some embodiments of the present disclosure, registering the first image and the second image includes: registering the first image and the second image by taking the second image as a fixed image and the first image as a floating image.

Some embodiments of the present disclosure further provide a computer device. The computer device includes: one or more processors; a memory; and one or more applications stored in the memory, wherein the one or more processors, when loading and executing the one or more applications, are caused to perform the method for generating the treatment plan according to the above embodiments.

Some embodiments of the present disclosure further provide a computer-readable storage medium storing a computer program thereon, wherein the computer program, when loaded and executed by a processor, causes the processor to perform the method for generating the treatment plan according to the above embodiments.

BRIEF DESCRIPTION OF DRAWINGS

For clearer descriptions of the technical solutions in the embodiments of the present disclosure, the following briefly introduces the accompanying drawings required for describing the embodiments. Apparently, the accompanying drawings in the following description show merely some embodiments of the present disclosure, and those skilled in the art may still derive other drawings from these accompanying drawings without creative efforts.

DETAILED DESCRIPTION OF THE INVENTION

Figure 1:
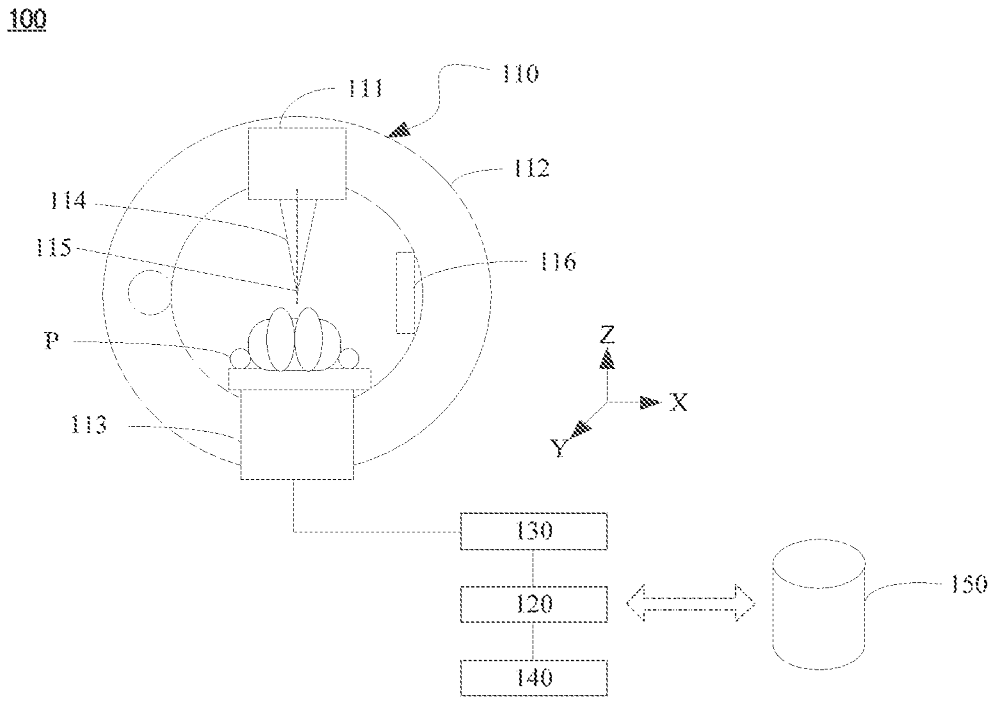
FIG. 1 is a schematic diagram of a scenario of a radiation device according to some embodiments of the present disclosure.

The technical solutions in the embodiments of the present disclosure will be clearly and completely described hereinafter with reference to the accompanying drawings in the embodiments of the present disclosure. Obviously, the described embodiments are merely some but not all embodiments of the present disclosure. Based on the embodiments of the present disclosure, all other embodiments derived by those skilled in the art without creative efforts shall fall within the protection scope of the present disclosure.

In the description of the present disclosure, it should be understood that orientation or positional relationships indicated by the terms "center," "longitudinal," "transverse," "length," "width," "thickness," "upper," "lower," "front," "back," "left," "right," "vertical," "horizontal," "top," "bottom," "inner," "outer," and the like are orientation or position relationship based on the accompanying drawings, and are merely intended to describe the present disclosure conveniently and simplify the description, rather than to indicate or imply that the referred apparatus or element must has a specific orientation or must be configured and operated at a specific orientation. Therefore, such terms should not be construed as limiting the present disclosure. Moreover, the terms "first," "second," and "third" are only for the purpose of description and should not be construed as indicating or implying relative importance or implicitly indicating the number of technical features indicated. Thus, the features defined by the terms "first," "second," and "third" may include one or more features explicitly or implicitly. In the description of the present disclosure, unless otherwise expressly defined, the term "a plurality of" means two or more.

In the present disclosure, the term "exemplary" is used to mean "being used as an example, for illustration, or explanation. Any embodiment described as being "exemplary" in the present disclosure may not necessarily be interpreted as more preferred or advantageous than other embodiments. The following description is given to implement and use the present disclosure by those skilled in the art. In the following description, details are shown for explanation. It should be understood that those of ordinary skill in the art can recognize that the present disclosure may also be implemented without using these specific details. In some embodiments, well-known structures and processes will not be elaborated in detail to avoid obscuring the description of the present disclosure by unnecessary details. Thus, the present disclosure is not intended to be limited to the shown embodiments, but should be consistent with the widest scope conforming to the principles and features disclosed herein.

It should be noted that as the method in the embodiments of the present disclosure is performed in a computer device, and processed objects of the computer device exist in the form of data or information, such as time, which is essentially time information. It can be understood that sizes, quantities, positions, and the like mentioned in subsequent embodiments are in the form of corresponding data for facilitating processing by the computer device, and specific details will not be described herein.

In some practices, in making the treatment plan, the patient is first positioned, that is, an affected part of the patient is positioned by a head positioning apparatus (such as a headstocks, a mask, and the like) or a body positioning apparatus (such as an abdominal compression band and the like), then computed tomography (CT) scanning is performed on the positioned patient to acquire a positioning image of the patient, and finally, the treatment plan of the patient is made based on the positioning image.

In the above processes, the treatment plan is made after the positioning image of the patient is acquired, and thus the treatment plan is made for long time.

Embodiments of the present disclosure provide a method for generating a treatment plan, a computer device, and a storage medium. The method for generating the treatment plan involves generating the treatment plan based on diagnostic image of the patient (i.e., an image taken for a not positioned patient), such that time for making the treatment plan by the user is shortened.

FIG. 1 exemplarily shows a radiation device 100. The radiation device 100 includes a radiation delivery apparatus 110, a master control system 120, a slave control system 130, a treatment planning system (TPS) 140, and a memory 150. In some embodiments, the radiation delivery apparatus 110, the master control system 120, the slave control system 130, the TPS 140, and the memory 150 are in wireless connection (for example, network connection) or wired connection, connected and/or communicated with each other in a combined manner.

In some embodiments, the radiation delivery apparatus 110 is an apparatus for delivering radiation for treatment. The radiation delivery apparatus 110 includes a radiation source 111, a rotating gantry 112, and a treatment bed 113.

The radiation source 111 is capable of generating or emitting a radiation beam 114. The radiation source 111 includes a linear accelerator and a treatment head loaded with a radioactive isotope source (such as a cobalt-60 radioactive source). There may be one or more (such as two) radiation sources 111.

The rotating gantry 112 is configured to support the radiation source 111 and is capable of driving the radiation source 111 to rotate around a rotation axis 115. A central axis of the rotation axis 115 is intersected with a central axis of the radiation beam 114 at an isocenter point.

The treatment bed 113 is configured to bear a patient P, and capable of translating in one or more of three orthogonal directions (X, Y, and Z directions shown in FIG. 1). In some embodiments, the treatment bed 113 may also rotate around any one or more of X, Y, and Z axes.

The position of the radiation source 111 relative to the patient and the orientation of radiation beam 114 relative to the patient may be achieved by controlling movements of the rotating gantry 112 and/or the treatment bed 113.

In some embodiments, the radiation delivery apparatus 110 may also include an image guidance apparatus 116 configured to provide a medical image for determining at least a part (such as a region of interest) of the patient. In some embodiments, the image guidance apparatus 116 may be, for example, a CT device, a cone-beam CT device, a positron emission computed tomography (PET) device, a volume CT device, a magnetic resonance imaging (MRI) device, or a combination thereof.

In some embodiments, the master control system 120 is configured to generate control instructions for one or more assemblies (such as the slave control system 130, the TPS 140, and the memory 150) of the radiation device 100. For example, the master control system 120 sends an instruction to the slave control system 130 to control the radiation delivery apparatus 110 to initiate an image guidance or treatment process. For example, the master control system 120 sends an instruction to the TPS 140 and acquires the treatment plan. In some embodiments, the instructions are input by the user (such as, a doctor) over a user interface of the master control system 120.

In some embodiments, the slave control system 130 is configured to control, in response to the control instruction generated by the master control system 120, the radiation delivery apparatus 110 to execute a corresponding action. For example, the slave control system 130 controls, based on a positioning instruction from the master control system 120, the movement of the treatment bed 113 of the radiation delivery apparatus 110 to position. For example, the slave control system 130 controls, based on a radiation delivery instruction from the master control system 120, the movement of the rotating gantry 112 of the radiation delivery apparatus 110 to achieve radiation delivery. For example, the slave control system 130 controls, based on an image guidance instruction from the master control system 120, the image guidance apparatus 116 of the radiation delivery apparatus 110 to perform image guidance on the patient to generate the medical image of the patient.

In some embodiments, the TPS 140 is configured to determine the treatment plan based on at least a portion of objects (such as, a tumor) in a planned image of the patient (the planned image is an image of the patient acquired prior to treatment using an imaging apparatus) and/or an image acquired based on the image guidance apparatus 116.

In some embodiments, both the master control system 120 and the TPS 140 are computer devices with graphical user interfaces (GUI). The computer device includes one or more processors, a memory, and one or more applications. For example, the one or more applications in the TPS 140 are stored in the memory, and the one or more processors, when loading and executing the one or more applications, are caused to perform the method for generating the treatment plan in the present disclosure. In some embodiments, the graphical user interface of the TPS 140 is configured to interact with the user for making the treatment plan.

In some embodiments, the master control system 120 and the TPS 140 are independent servers, or a server network or server cluster composed of servers. For example, the computer device in the embodiments of the present disclosure includes, but is not limited to a computer, a network host, a single network server, a multi-network-server set, or a cloud server composed of a plurality of servers. The cloud server is composed of a large number of computers or network servers based on cloud computing.

In some embodiments, the master control system 120 and the TPS 140 are a general-purpose computer device or a special-purpose computer device. In the specific implementation, the computer device may be a desktop computer, a portable computer, a network server, a personal digital assistant (PDA), a mobile phone, a tablet computer, a wireless terminal device, a communication device, an embedded device, and the like, and the type of the computer device is not limited in the embodiments.

In some embodiments, the slave control system 130 is a computer device, and the computer device includes a processor, a storage device, an input/output (I/O) and communication port. The processor 310 includes a microcontroller, a microprocessor, a reduced instruction set computer (RISC), an application specific integrated circuit (ASIC), an application specific instruction-set processor (ASIP), a central processing unit (CPU), a graphics processing unit (GPU), a physical processing unit (PPU), a single-chip microcomputer, a digital signal processor (DSP), a field programmable gate array (FPGA), an advanced reduced instruction set machine (ARM), a programmable logic devices (PLD), any circuit or processor capable of achieving at least one function, or any combination thereof.

For the radiation device 100 in the embodiments, in performing the radiation therapy, the master control system 120 acquires the treatment plan for tumor treatment of the patient from the TPS 140, and issues the acquired treatment plan and the control instructions to the slave control system 130, and the slave control system 130 controls, based on treatment plan information and the control instructions, the radiation delivery apparatus 110 to deliver the radiation therapy to the tumor of the patient.

In some embodiments, the radiation device 100 further includes one or more other computer devices capable of processing data, for example, an oncology information system (OIS). The OIS is configured to schedule the treatment plan of the patients and store treatment data (such as image data of the patient, treatment plan data, radiation delivery information, and the like).

The memory 150 stores data, instructions, and/or any other information. In some embodiments, the memory 150 stores data acquired from the TPS 140. In some embodiments, the memory 150 stores data and/or instructions used by the master control system 120 to perform the exemplary method in the present disclosure. In some embodiments, the memory 150 includes a high-capacity memory, a removable memory, a volatile read-write memory, a read-only memory (ROM), or any combination thereof. The exemplary high-capacity memory includes disks, optical disks, solid-state drives, and the like. The exemplary removable memory includes flash drives, floppy disks, optical disks, memory cards, compressed disks, magnetic tapes, and the like. The exemplary volatile read-write memory includes a random access memory (RAM). The exemplary RAM includes a dynamic random access memory (DRAM), a double data rate synchronous dynamic random-access memory (DDR SDRAM), a static random access memory (SRAM), a thyristor random access memory (T-RAM), a zero-capacitor random access memory (Z-RAM), and the like. The exemplary ROM includes a mask ROM (MROM), a programmable ROM (PROM), an erasable programmable ROM (EPROM), an electrically erasable programmable ROM (EEPROM), a compact disc ROM (CD-ROM), a digital multifunctional disc ROM, and the like. In some embodiments, the memory 150 is implemented on a cloud platform. For example, the cloud platform includes private clouds, public clouds, hybrid clouds, community clouds, distributed clouds, internal clouds, multi-layer clouds, or any combination thereof.

In some embodiments, the memory 150 is connected to a network to communicate with one or more assemblies (such as the master control system 120, the TPS 140, and the OIS) of the radiation device 100. The one or more assemblies of the radiation device 100 access data or instructions stored in the memory 150 over a network. In some embodiments, the memory 150 is directly connected to or communicated with one or more assemblies (such as the master control system 120, the TPS 140, and the OIS) of the radiation device 100. In some embodiments, the memory 150 is a part of the master control system 120, the TPS 140, and the OIS.

It should be noted that the schematic diagram of the scenario of the radiation device shown in FIG. 1 is only an example. The radiation device and the scenario described in the embodiments of the present disclosure are for clearer description of the technical solutions in the embodiments of the present disclosure, and do not constitute a limitation to the technical solutions provided by the embodiments of the present disclosure. Those of ordinary skill in the art may know that with the evolution of the radiation device and the emergence of new service scenarios, the technical solution provided by the embodiments of the present disclosure is also applicable to similar technical problems.

Firstly, some embodiments of the present disclosure provide a method for generating a treatment plan. An execution subject of the method for generating the treatment plan is the processor in the computer device. The method for generating the treatment plan includes:

acquiring a first image of a target object, wherein the first image does not contain positioning information of the target object; generating a first treatment plan for the target object based on the first image; acquiring a second image of the target object, wherein the second image contains the positioning information of the target object; registering the first image and the second image; and generating a second treatment plan for the target object by updating the first treatment plan in response to a registration result.

Figure 2:
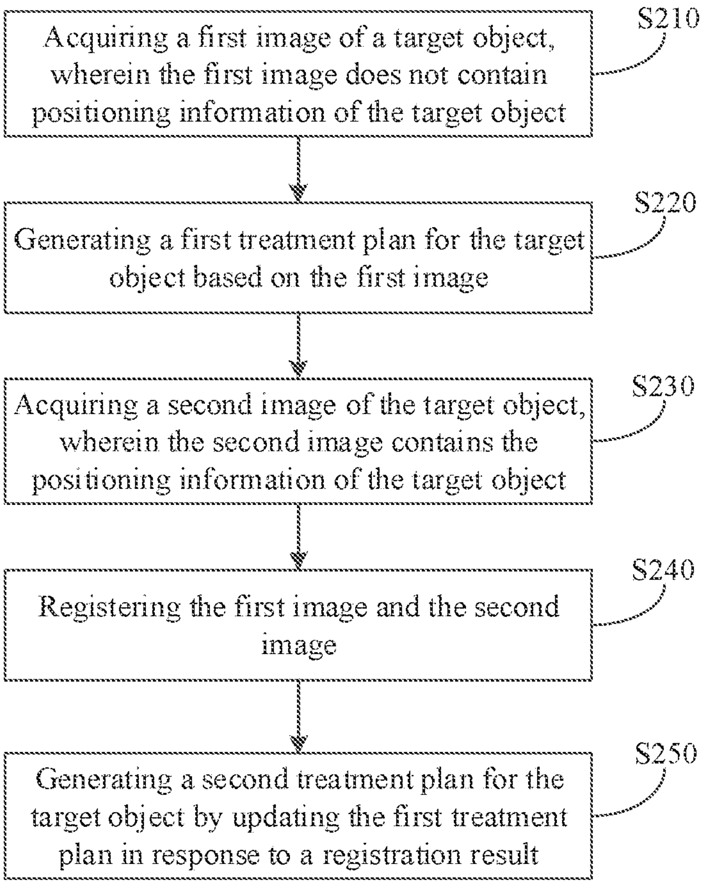
FIG. 2 is a schematic flowchart of an embodiment of a method for generating a treatment plan according to some embodiments of the present disclosure.

FIG. 2 is a schematic flowchart of some embodiments of a method for generating a treatment plan according to some embodiments of the present disclosure. As shown in FIG. 2, the method for generating the treatment plan includes S210-S250 as follows. The details are as follows.

In S210, an image of a target object is acquired.

The processor in the computer device for performing the method for generating the treatment plan in the present disclosure acquires the first image of the target object. The first image does not contain positioning information of the target object.

In the embodiments of the present disclosure, the first image is acquired by scanning the target object by an imaging apparatus in the case that the target object is not positioned. For example, the first image is acquired by scanning the target object by the imaging apparatus in the case that the target object does not wear a heat gantry or is not positioned by a mask or an abdominal pressure band. Generally, the first image that does not contain the positioning information of the target object is also referred to as a diagnostic image, that is, the image is an image for diagnosing a tumor of the patient by a doctor.

The first image is generally a CT image, an MRI image, a PET image, or other types of images of a patient.

In some embodiments, the positioning information includes, for example, a laser-lamp-marked point, a head gantry marking point, a lead point, and the like. Generally, a positional association between a target tumor and a radiation device is established based on the positioning information.

In the embodiments of the present disclosure, the target object generally refers to a patient who needs radiation therapy, or a part (such as a tumor region or a region of interest) of the patient.

In S220, a first treatment plan for the target object is generated based on the first image.

The processor in the computer device for performing the method for generating the treatment plan in the present disclosure generates the first treatment plan for the target object based on the first image upon acquiring the first image.

Generally, the treatment plan is generated by a software program of the computer device (that is, TPS) for performing the method for generating the treatment plan in the present disclosure. In order to generate the treatment plan, the TPS is communicated with the imaging apparatus to access the image of the target object (for example, acquire the first image), the image of the target object requires to be outlined or segmented upon acquiring the image of the target object. In some embodiments, one or more organs at risk, such as healthy tissue around or adjacent to the target tumor, may need to be depicted. Therefore, in the case where the organ at risk is close to the target tumor, the organ at risk and the target tumor are outlined or segmented. The outlining or segmentation is performed manually (for example, by the doctor, a dosimetrist, or a medical worker) or automatically (for example, by dedicated segmentation software or treatment planning software). Upon competition of image segmentation, the doctor, the dosimetrist, or the medical worker determines the radiation dose to be applied to the target tumor, and any maximum dose receivable by the organ at risk adjacent to the target tumor. Upon determination of the radiation dose for each anatomical structure (such as the target tumor and the organs at risk), a process called reverse planning is performed to determine one or more treatment plan parameters that can achieve desired dose distribution. Results of the reverse planning form a treatment plan stored in the memory 150 or the TPS 140.

In some embodiments, the treatment plan parameters include treatment parameters. In some embodiments, the treatment parameters include parameters such as target coordinates, a collimator size, a radiation duration, an arc angle, and the like. In some embodiments, the treatment parameters also include a beam angle, a beam intensity, a collimator position, and the like.

In some embodiments, the treatment plan parameters also include an image guidance parameter, such as a radiograph-taken point position parameter. For example, for frameless treatment (that is, a treatment manner in which the target object is fixed with the mask) and body treatment (for example, lung and abdomen treatment with respect to head treatment), the output treatment plan parameters include the image guidance parameter.

In S230, a second image of the target object is acquired, wherein the second image contains the positioning information of the target object.

The processor in the computer device for performing the method for generating the treatment plan in the present disclosure acquires the second image of the target object. The second image contains the positioning information of the target object.

In the embodiments of the present disclosure, the second image is acquired by scanning the target object by the imaging apparatus in the case that the target object is positioned. For example, the second image is acquired by scanning the target object by the imaging apparatus in the case that the target object wears the heat gantry or is positioned by the mask or the abdominal pressure band. Generally, the second image that contains the positioning information of the target object is also referred to as a positioning image, that is, the image is an image acquired by scanning in the case that the target object is positioned.

In S240, the first image and the second image are registered.

The processor in the computer device for performing the method for generating the treatment plan in the present disclosure registers the first image and the second image upon acquiring the second image, such that a deviation between the first image and the second image is determined.

In some embodiments, the deviation between the first image and the second image generally includes a positional deviation of regions of interest (such as the target tumor and/or the organ at risk) in the two images. Generally, a rotation offset amount and a translation offset amount are used to characterize the positional deviation of the two images.

The translation offset amount includes linear offset amounts of the two images in three orthogonal directions (such as linear offset amounts of the two images in X, Y, and Z directions); and the rotation offset amount includes offset amounts of the two images in rotation directions around three orthogonal axes (such as offset amounts of the two images in rotation directions around the X, Y, and Z axes).

A registration process generally includes: translating and/or rotating the floating image based on registration regions to be registered by taking one of the two images as a fixed image and the other as a floating image, such that the registration regions in the two images are completely coincided. In this process, the amount translated and/or rotated by the floating image is a deviation amount between the two images, which is output as a registration result.

In S250, a second treatment plan for the target object is generated by updating the first treatment plan in response to the registration result.

Upon acquisition of the registration result of the two images, the processor of the computer device for performing the method for generating the treatment plan in the present disclosure modifies the corresponding treatment parameters in the first treatment plan (for example, the target site position coordinates, beam angle, and the like) based on the rotation offset amount and/or the translation offset amount between the two images, such that the treatment parameters in the first treatment plan match the position(s) of the target tumor and/or the organ at risk in the second image to generate the second treatment plan for the target object.

Modifying the corresponding parameters in the first treatment plan refers to modifying, based on the deviation amount between the first image and the second image, the treatment parameters in the first treatment plan affected by the above deviation amount, for example, the target site position coordinates, the beam angle, and the like.

Meanwhile, as the second image is the positioning image of the target object, by updating the first treatment plan, the treatment parameters in a treatment plan coordinate system are converted to treatment parameters in a radiation device coordinate system, such that the second treatment plan performed on the radiation device is generated.

In some embodiments, the first and second images are images with the same modality (for example, both the first and second images are CT images or MRI images), or images with different modalities (for example, the first image is the CT image, and the second image is the MRI image). It may be understood that in the embodiments of the present disclosure, the image modalities are not limited to CT images and MRI images, and the images may also be images of other modalities, such as PET images.

In some embodiments, both the first image and the second image are images of the target object acquired prior to a treatment stage. In some embodiments, both the first image and the second image are images of the target object acquired in a treatment planning stage.

Therefore, in the method for generating the treatment plan in the embodiments of the present disclosure, the first treatment plan for the target object is generated based on diagnostic image data, and then the executable second treatment plan is generated by updating the first treatment plan based on acquired positioning image data of the target object and the deviation between the positioning image data and the diagnostic image data. In the process, as the step of generating the first treatment plan and the step of acquiring the positioning image can be performed simultaneously, the time for making the treatment plan by the user can be greatly shortened.

Figure 3:
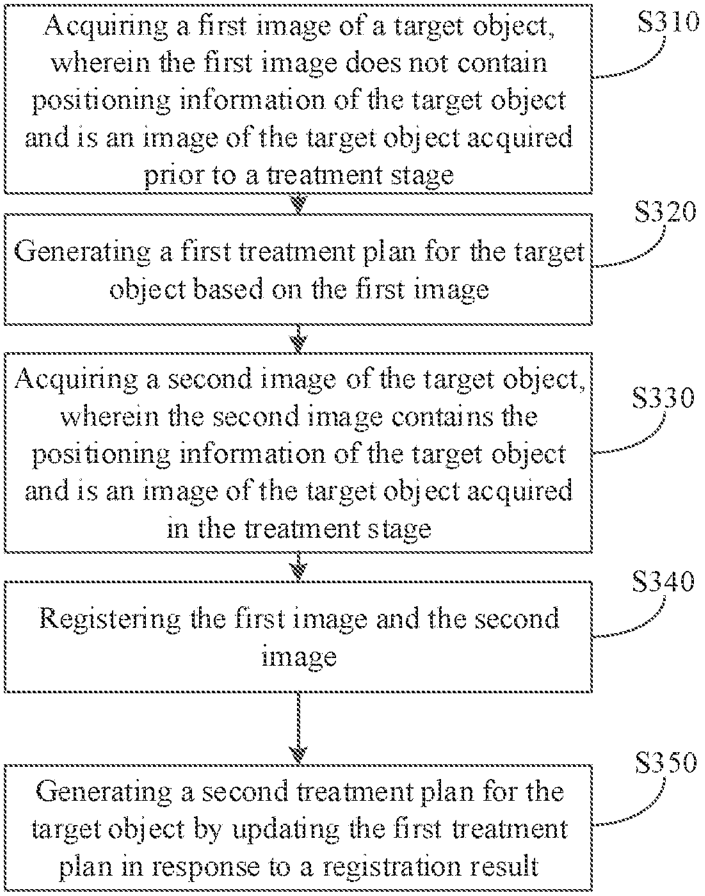
FIG. 3 is a schematic flowchart of another embodiment of a method for generating a treatment plan according to some embodiments of the present disclosure.

FIG. 3 is a schematic flowchart of another embodiment of a method for generating a treatment plan according to some embodiments of the present disclosure. As shown in FIG. 3, the method for generating the treatment plan includes S310-S350. In the embodiments, S320, S340, and S350 are the same as S220, S240, and S250 in the embodiments shown in FIG. 2, and thus will not be repeated herein.

As shown in S310 and S330 in FIG. 3, in the embodiments, the first image is an image of the target object acquired prior to the treatment stage, and the second image is an image of the target object acquired in the treatment stage. The treatment stage includes a treatment positioning stage.

The second treatment plan is generated by acquiring the positioning image of the target object in the treatment stage and updating the first treatment plan based on the positioning image of the target object in the treatment stage to avoid the problem that the position(s) of the target tumor and/or the organ at risk change(s) due to a deviation between the position of the patient on a treatment bed in the treatment positioning stage and the position of the patient on a diagnostic bed prior to treatment, and thus the first treatment plan is not adapted to the actual condition of the target tumor in the treatment stage. By updating the first treatment plan based on the positioning images of the target object in the treatment stage, the first treatment plan adapts to changes in the position(s) of the target tumor and/or the organ at risk, such that a treatment accuracy is improved.

In some embodiments, prior to acquiring the second image of the target object, the method further includes: instructing, by outputting the first treatment plan only containing the image guidance parameter, the radiation device to perform image guidance on the target object to generate the second image of the target object.

Upon generating the first treatment plan, the processor of the computer device (i.e., the TPS 140) for performing the method for generating the treatment plan in the present disclosure instructs, by outputting the first treatment plan only containing the image guidance parameter to the master control system 120, the image guidance apparatus 116 of the radiation delivery apparatus 110 to perform image guidance on the target object to generate the second image. The image guidance parameter includes the radiograph-taken point position parameter.

Upon receiving the first treatment plan only containing the image guidance parameter, the master control system 120 controls the radiation delivery apparatus 110 to move the treatment bed based on the radiograph-taken point position parameter, such that the radiograph-taken point position of the positioned target object is coincided with an imaging center point of the image guidance apparatus 116, and controls the image guidance apparatus 116 to perform image guidance on the target object to generate the second image.

In some embodiments, the image guidance apparatus 116 of the radiation delivery apparatus 110 may be a CT apparatus, a cone-beam CT apparatus, an MRI apparatus, and the like. Correspondingly, the generated second image may be a CT image, a CBCT image, an MRI image, and the like. In the embodiments of the present disclosure, the second image is preferably the CBCT image.

In the embodiments of the present disclosure, as the TPS 140 outputs the first treatment plan only containing the image guidance parameter to the master control system 120 upon generating the first treatment plan, the master control system 120 does not continue to control radiation delivery after the image guidance apparatus 116 of the radiation delivery apparatus 110 completes image guidance to generate the second image, such that the target object is prevented from receiving incorrect radiation delivery.

In some embodiments, the TPS 140 registers the first image and the CBCT image upon acquiring the CBCT image of the patient. In registration, by taking the CBCT image as a fixed image and the first image as a floating image, the deviation between the first image and the CBCT image is determined, and then the second treatment plan is generated by modifying the treatment parameters in the first treatment plan based on the determined deviation. The processes of modifying the parameters in the first treatment plan and generating the second treatment plan are the same as the description in the embodiments shown in FIG. 2, and thus will not be repeated herein.

By adopting the method for generating the treatment plan in the embodiments of the present disclosure, the adaptive radiation treatment of the patient between different treatment fractions can be achieved. That is, the treatment plan acquired by the method for generating the treatment plan in the embodiments of the present disclosure can adapt to changes in the position(s) of the target tumor and/or the organ at risk at different fractions, such that the accuracy and precision of treatment are ensured.

Figure 4:
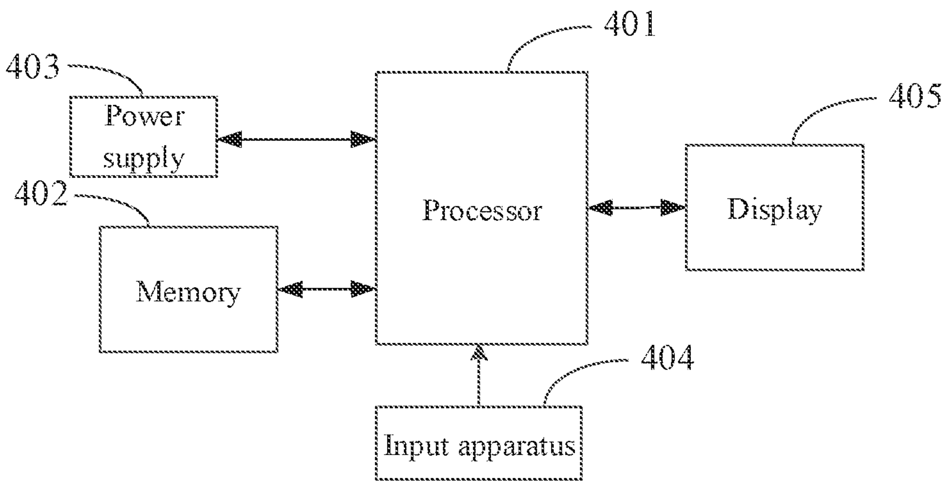
FIG. 4 is a schematic structural diagram of an embodiment of a computer device according to some embodiments of the present disclosure.

Some embodiments of the present disclosure further provide a computer device. The computer device includes: one or more processors; a memory; and one or more applications stored in the memory. The one or more processors, when loading and executing the one or more applications, are caused to perform the method for generating the treatment plan in any of embodiments of the method for generating the treatment plan. Some embodiments of the present disclosure further provide a computer device. As shown in FIG. 4, FIG. 4 shows a structural schematic diagram of a computer device in the embodiments of the present disclosure. The details are as follows.

The computer device includes assemblies such as a processor 401 having one or more processing cores, a memory 402 of one or more computer-readable storage media, a power supply 403, and an input apparatus 404. It may be understood by those skilled in the art that the computer device structure shown in FIG. 4 does not constitute a limitation to the computer device. The computer device may include more or fewer assemblies than those shown in the drawing, or combine some components, or use different component arrangements.

The processor 401 is a control center of the computer device, and connects various parts of the entire computer device through various interfaces and lines. By running or executing software programs and/or modules stored in the memory 402 and invoking data stored in the memory 402, various functions and data processing of the computer device are implemented, such that the computer device is monitored.

In some embodiments, the processor 401 includes one or more processing cores. In some embodiments, the processor 401 is integrated as an application processor and a modulation and demodulation processor. The application processor mainly processes an operating system, a user interface, an application, and the like, and the modulation and demodulation processor mainly processes wireless communication. It may be understood that the above modulation and demodulation processor may also not be integrated into the processor 401.

The memory 402 is configured to store software programs and modules, and the processor 401 executes various functional applications and data processing by running the software programs and the modules stored in the memory 402. The memory 402 mainly includes a program storage region and a data storage region. The program storage region stores the operating system, an application required for at least one function (such as a sound playing function and an image playing function), and the like. The data storage region stores data created based on the use of the computer device, and the like. In addition, the memory 402 includes a high-speed random access memory and a non-volatile memory, such as at least one of a disk storage device, a flash memory device, or other volatile solid-state storage devices. Correspondingly, the memory 402 also includes a memory controller to provide access to the memory 402 by the processor 401.

The computer device also includes the power supply 403 that supplies power to various assemblies. In some embodiments, the power supply 403 is logically connected to the processor 401 through a power supply management system, such that the functions, such as management of charging, discharging, and power consumption are achieved through the power supply management system. The power supply 403 further includes one or more direct current or alternating current power supplies, a recharging systems, a power failure detection circuit, a power converter or an inverter, a power status indicator, and any other assemblies.

The computer device also includes an input apparatus 404. The input apparatus 404 is configured to receive input digital or character information, and generate keyboard, mouse, joystick, optical, or trackball signal input related to user settings and function control.

Although not shown, a display apparatus 405 is further included in the computer device. The display apparatus 405 is a display, and thus will not be repeated herein. Specifically, in the embodiments, the processor 401 in the computer device loads, according to the following instructions, executable files corresponding to one or more application processes into the memory 402, and the processor 401 runs the applications stored in the memory 402 to achieve various functions as follows:

acquiring a first image of a target object, wherein the first image does not contain positioning information of the target object;

generating a first treatment plan for the target object based on the first image;

acquiring a second image of the target object, wherein the second image contains the positioning information of the target object;

registering the first image and the second image; and generating a second treatment plan for the target object by updating the first treatment plan in response to a registration result.

Those of ordinary skill in the art may understand that all or part of the processes in the various methods of the above embodiments can be performed by instructions, or by controlling related hardware through instructions. The instructions may be stored in a computer-readable storage medium, and loaded and executed by the processor.

For this purpose, some embodiments of the present disclosure provide a non-volatile computer-readable storage medium. The storage medium may include a read-only memory (ROM), a random access memory (RAM), a disk or an optical disc, and the like. A computer program is stored on the storage medium, and the computer program is loaded by a processor to perform any of the methods for generating the treatment plans in the embodiments of the present disclosure. For example, the computer program, when loading and executing by the processor, causes the processor to perform:

acquiring a first image of a target object, wherein the first image does not contain positioning information of the target object;

generating a first treatment plan for the target object based on the first image;

acquiring a second image of the target object, wherein the second image contains the positioning information of the target object;

registering the first image and the second image; and generating a second treatment plan for the target object by updating the first treatment plan in response to a registration result.

In the above embodiments, the description of each embodiment has its own emphasis. The parts not detailed in an embodiment may refer to the detailed description for other above embodiments and are not repeated here.

In specific implementation, the above various structures are implemented as independent entities, or are arbitrarily combined to be implemented as the same or several entities. The specific implementations of the above various structures may refer to the above method embodiments, and thus are not repeated here.

The specific implementations of the above various operations may refer to the above embodiments, and thud are not repeated here.

The method for generating the treatment plan, the computer device, and the storage medium in the embodiments of the present disclosure are described in detail herein. Specific examples are used herein to explain the principles and embodiments of the present disclosure. The descriptions of the above embodiments are only used to help understand the method and the core idea of the present disclosure. Meanwhile, those skilled in the art will be changed in the specific embodiments and the application scope according to the idea of the present disclosure. In summary, the content of the Specification should not be understood as a limitation to the present disclosure.

What is claimed is:

1. A radiation therapy control method, applied to a radiation device, wherein the radiation device comprises a radiation delivery apparatus, a master control system, and a treatment planning system, both the radiation delivery apparatus and the treatment planning system being connected to the master control system; and the method comprising:

acquiring, by the treatment planning system, a first image of a target object, wherein the first image does not contain positioning information of the target object, and the first image is a diagnostic image acquired in a case where the target object is not positioned by a positioning apparatus; and the positioning apparatus comprises a head frame, a mask and other head fixation devices, or a body membrane and other body positioning devices;

generating, by the treatment planning system, a first treatment plan for the target object based on the first image;

acquiring, by the treatment planning system, a second image of the target object, wherein the second image contains the positioning information of the target object, and the second image is a positioning image acquired in a case where the target object is positioned by the positioning apparatus;

registering, by the treatment planning system, the first image and the second image;

generating, by the treatment planning system, a second treatment plan for the target object by updating the first treatment plan in response to a registration result;

acquiring, by the master control system, the second treatment plan generated by the treatment planning system, and transmitting a control instruction to the radiation delivery apparatus; and delivering, by the radiation delivery apparatus, radiation therapy to a tumor of a patient based on the control instruction.

2. The radiation therapy control method according to claim 1, wherein the registration result comprises a rotation offset amount and a translation offset amount.

3. The radiation therapy control method according to claim 2, wherein generating, by the treatment planning system, the second treatment plan for the target object by updating the first treatment plan in response to the registration result comprises:

generating, by the treatment planning system, the second treatment plan for the target object by modifying corresponding treatment parameters in the first treatment plan based on the rotation offset amount and the translation offset amount.

4. The radiation therapy control method according to claim 1, wherein both the first image and the second image are images of the target object acquired prior to a treatment stage.

5. The radiation therapy control method according to claim 1, wherein the first image is an image of the target object acquired prior to a treatment stage; and the second image is an image of the target object acquired in the treatment stage.

6. The radiation therapy control method according to claim 5, wherein the first treatment plan comprises an image guidance parameter and first treatment parameters; and prior to acquiring, by the treatment planning system, the second image of the target object, the method further comprises:

instructing, by the treatment planning system, the radiation device to perform image guidance on the target object to generate the second image of the target object by outputting the first treatment plan only containing the image guidance parameter.

7. The radiation therapy control method according to claim 5, wherein the second image is a cone beam computed tomography (CBCT) image of the target object acquired in the treatment stage.

8. The radiation therapy control method according to claim 5, wherein registering, by the treatment planning system, the first image and the second image comprises:

registering, by the treatment planning system, the first image and the second image by taking the second image as a fixed image and the first image as a floating image.

9. The radiation therapy control method according to claim 1, wherein the registration result comprises a rotation offset amount or a translation offset amount.

10. The radiation therapy control method according to claim 9, wherein generating, by the treatment planning system, the second treatment plan for the target object by updating the first treatment plan in response to the registration result comprises:

generating, by the treatment planning system, the second treatment plan for the target object by modifying corresponding treatment parameters in the first treatment plan based on the rotation offset amount or the translation offset amount.

11. A radiation therapy control apparatus, comprising: a radiation delivery apparatus, a master control system, and a treatment planning system, wherein both the radiation delivery apparatus and the treatment planning system are connected to the master control system;

the treatment planning system is configured to:

acquire a first image of a target object, wherein the first image does not contain positioning information of the target object, and the first image is a diagnostic image acquired in a case where the target object is not positioned by a positioning apparatus; and the positioning apparatus comprises a head frame, a mask and other head fixation devices, or a body membrane and other body positioning devices;

generate a first treatment plan for the target object based on the first image;

acquire a second image of the target object, wherein the second image contains the positioning information of the target object, and the second image is a positioning image acquired in a case where the target object is positioned by the positioning apparatus;

register the first image and the second image; and generate a second treatment plan for the target object by updating the first treatment plan for controlling radiation delivery in response to a registration result, the master control system is configured to acquire the second treatment plan generated by the treatment planning system, and transmit a control instruction to the radiation delivery apparatus; and the radiation delivery apparatus is configured to deliver radiation therapy to a tumor of a patient based on the control instruction.

12. The radiation therapy control apparatus according to claim 11, wherein the registration result comprises a rotation offset amount and a translation offset amount.

13. The radiation therapy control apparatus according to claim 12, wherein the treatment planning system is specifically configured to:

generate the second treatment plan for the target object by modifying corresponding treatment parameters in the first treatment plan based on the rotation offset amount and the translation offset amount.

14. The radiation therapy control apparatus according to claim 11, wherein both the first image and the second image are images of the target object acquired prior to a treatment stage.

15. The radiation therapy control apparatus according to claim 11, wherein the first image is an image of the target object acquired prior to a treatment stage; and the second image is an image of the target object acquired in the treatment stage.

16. The radiation therapy control apparatus according to claim 15, wherein the first treatment plan comprises an image guidance parameter and first treatment parameters; and the treatment planning system is specifically configured to:

instruct, by outputting the first treatment plan only containing the image guidance parameter, a radiation device to perform image guidance on the target object to generate the second image of the target object.

17. The radiation therapy control apparatus according to claim 15, wherein the second image is a cone beam computed tomography (CBCT) image of the target object acquired in the treatment stage.

18. The radiation therapy control apparatus according to claim 15, wherein the treatment planning system is specifically configured to:

register the first image and the second image by taking the second image as a fixed image and the first image as a floating image.

* * * * *